United States Patent [19]

Freidinger et al.

[11] Patent Number: 4,703,034

[45] Date of Patent: Oct. 27, 1987

[54] NOVEL CYCLIC TETRAPEPTIDE

[75] Inventors: Roger Freidinger, Hatfield; Ruth F. Nutt, Green Lane; Terry A. Lyle, Lederach, all of Pa.; Richard Saperstein, Edison, N.J.

[73] Assignee: Merck & Co., Inc., Rahway, N.J.

[21] Appl. No.: 856,252

[22] Filed: Apr. 28, 1986

[51] Int. Cl.$^4$ ............... A61K 37/02; C07K 5/12; C07K 7/26
[52] U.S. Cl. ................... 514/11; 514/806; 530/317; 530/318; 530/311
[58] Field of Search ............... 514/11, 806; 530/317, 530/318, 311

[56] References Cited

U.S. PATENT DOCUMENTS 4,310,518  1/1982  Freidinger et al. ............... 514/11

Primary Examiner—Delbert R. Phillips
Attorney, Agent, or Firm—David L. Rose; Michael C. Sudol, Jr.

[57] ABSTRACT

There is disclosed a series of novel cyclic tetrapeptides related to somatostatin. The compounds have surprisingly been found to have the activity of increasing blood glucose when administered. The compounds are prepared using the solid phase or mixed anhydride synthesis methods and compositions and methods utilizing the novel compounds are also disclosed.

13 Claims, No Drawings

NOVEL CYCLIC TETRAPEPTIDE

BACKGROUND OF THE INVENTION

Somatostatin and derivatives of somatostatin have been investigated for many years for their ability to lower blood glucose and glucagon levels and thus their possible utility in treating diabetes, a condition characterized by frequent uncontrolled increases in blood glucose levels. None of the work in the somatostatin analogs however suggested that modifications could lead to the unexpected development of a cyclic tetrapeptide which raised blood glucose and glucagon levels.

SUMMARY OF THE INVENTION

The instant invention is concerned with novel cyclic tetrapeptide compounds related to somatostatin which have the ability to raise blood glucose and glucagon. Thus, it is an object of this invention to describe such novel compounds. A further object is to describe processes for the preparation of such compounds. A still further object is to describe the ability of such compounds to raise blood glucose and glucagon levels. A still further object is to describe compositions containing such novel cyclic tetrapeptides as the active ingredient thereof. Further objects will become apparent from a reading of the following description.

DESCRIPTION OF THE INVENTION

The novel cyclic tetrapeptides of the instant invention are best realized in the following structural formulae:

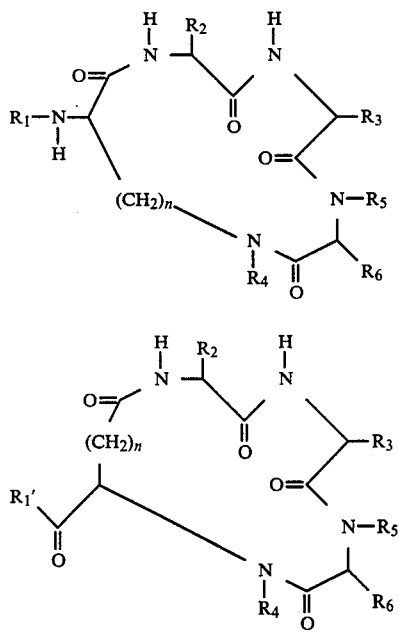

wherein:

$n$ is 0 to 4;

$R_1$ is phenylloweralkanoyl, or an amino acid

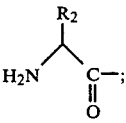

$R_1'$ is phenylloweralkylamino, or an amino acid

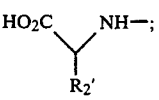

$R_2$ and $R_2'$ are loweralkyl, benzyl, naphthylmethyl, indolylmethyl, substituted benzyl where the substituent may be one or two of loweralkyl, halogen, hydroxy, amino, nitro or loweralkoxy; and loweralkyl substituted with a 5- or 6-membered heterocyclic ring;

$R_3$ is 3-indolylmethyl, naphthylmethyl or substituted 3-indolylmethyl wherein the substituent may be loweralkyl, loweralkoxy, or halogen;

$R_4$ and $R_5$ are independently hydrogen or methyl $R_6$ is aminocyclohexylmethyl, aminomethylbenzyl or

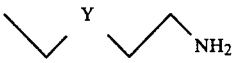

wherein Y is $(CH_2)_m$ and $m$ is 0, 1 or 2 or sulfur such that the sulfur may be in any position along the chain.

The term "loweralkyl" when used in the instant application is intended to represent those alkyl groups either straight or branched chain, which have from 1–5 carbon atoms. Examples of such alkyl groups are methyl, ethyl, propyl, iso-propyl, butyl, sec-butyl, pentyl and the like.

The term "loweralkoxy" is intended to include those alkoxy groups of from 1–5 carbon atoms, in either a straight or branched chain. Examples of such alkoxy groups are methoxy, ethoxy, propoxy, isopropoxy, butoxy, tert-butoxy, pentoxy and the like.

The term "halogen" or "halo" is intended to include fluorine, chlorine, bromine and iodine.

The term "5- or 6-membered heterocyclic ring" is intended to include those 5- and 6-membered heterocycles with 1- or 2-heteroatoms selected from oxygen, nitrogen and sulfur. Exemplary of such heterocycles is imidazole, furan, thiazole, pyrazole, pyridine and the like.

In the instant compounds there are several asymmetric centers which will lead to the existence of optical isomers for such compounds. In the instant invention, for each of the asymmetric centers of the various amino acids which make up the instant cyclic tetrapeptides, both the D and L configurations are intended to be encompassed.

The instant compounds have been found to have the unexpected effect of increasing blood glucose and glucagon levels. Thus, such compounds will find utility in those situations where blood glucose levels are subnormal such as in cases of hypoglycemia and hyperinsulinemia, prevalent in diabetics when the usually maintained balance of diet, exercise and exogeneous insulin is upset. This can lead to increased insulin levels, decreased blood glucose levels, which can result in insulin shock characterized by faintness, weakness, tremulousness, palpitation, headache, confusion and personality changes which if not attended to may result in the patient falling into a coma. Similar symptoms occur in cases of insulinoma, a tumor of the pancreatic inlet cells which results in increased insulin production.

It will be appreciated by those skilled in the art that when $R_2$ is benzyl, $R_3$ is indolylmethyl, $R_5$ is hydrogen, and $R_6$ is $CH_2—CH_2—CH_2CH_2NH_2$, the 7, 8, and 9 amino acids of somatostatin (-Phe-Trp-Lys-) are represented, and the $R_1$ or $R_1'$ containing bridge has taken the place of the remainder of the somatostatin amino acids. Thus, using the above definitions of the substituent groups, the following representative cyclic tetrapeptide analogs of somatostatin are formed in structures I and II:

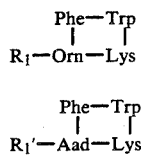

The preferred embodiments of the cyclic tetrapeptides of this invention are realized in the foregoing structural formula.

n is 3;
$R_1$, $R_1'$ and $R_2$ are as defined above;
$R_3$ is 3-indolylmethyl;
$R_4$ and $R_5$ are hydrogen; and
$R_6$ is $—CH_2—CH_2—CH_2CH_2NH_2$.

The preferred $R_2$ groups are loweralkyl, benzyl or substituted benzyl where the substituent is loweralkyl, halogen, hydroxy, amino, nitro or alkoxy.

The preferred $R_1$ groups are phenylloweralkanoyl, or an amino acid wherein $R_2$ is benzyl and the preferred $R_1'$ groups are phenylloweralkylamino or an amino acid where $R_2$ is benzyl.

Included within these preferred compounds are:
Cyclo-(D-Trp-Lys-δ-Aad(NHCH$_2$Ph)-Phe)
Cyclo-(D-Trp-Lys-δ-Aad(NHCH$_2$CH$_2$Ph)-Phe)
Cyclo-(D-Trp-Lys-δ-Aad(NHCH$_2$CH$_2$CH$_2$Ph)-Phe)
Cyclo-(D-Trp-Lys-δ-D-Aad(NHCH$_2$Ph)-Phe)
Cyclo-(D-Trp-Lys-δ-D-Aad(NHCH$_2$CH$_2$Ph)-Phe)
Cyclo-(D-Trp-Lys-δ-D-Aad(NHCH$_2$CH$_2$CH$_2$Ph)-Phe)
Cyclo-(Trp-Lys-δ-Orn(COCH$_2$Ph)-Phe)
Cyclo-(Trp-Lys-δ-Orn(COCH$_2$CH$_2$Ph)-Phe)
Cyclo-(Trp-Lys-δ-Orn(COCH$_2$CH$_2$CH$_2$Ph)-Phe)
Cyclo-(D-Trp-Lys-δ-Orn(COCH$_2$Ph)-Phe)
Cyclo-(D-Trp-Lys-δ-Orn(COCH$_2$CH$_2$CH$_2$Ph)-Phe)
Cyclo-(D-Trp-Lys-δ-Orn(COCH$_2$CH$_2$Ph)-Phe)
Cyclo-(Trp-Lys-δ-Orn(BOC-Phe)-Phe)
Cyclo-(D-Trp-Lys-δ-Orn(BOC-Phe)-Phe)
Cyclo-(D-Trp-Lys-δ-Orn(BOCCH$_2$-Phe)-Phe)
Cyclo-(D-Trp-Lys-δ-Orn(Phe)-Phe)
Cyclo-(Trp-Lys-δ-Orn(Phe)-Phe)
Cyclo-(Trp-Lys-δ-Orn(D-Phe)-Phe)
Cyclo-(Trp-Lys-δ-Orn(BOC-D-Phe)-Phe)
Cyclo-(D-Trp-Lys-δ-Orn(D-Phe)-Phe)

In the instant application several abbreviated designations are used for the amino acid components, certain preferred protecting groups, reagents and solvents. The meanings of such abbreviated designations are given in Table I.

TABLE I

| Abbreviated Designation | |
|---|---|
| | Amino Acid |
| Lys | L-lysine |
| Phe | L-phenylalanine |
| Trp | L-tryptophan |
| D-Trp | D-tryptophan |
| AChxAla | aminocyclohexylalanine |
| AmPhe | aminomethylphenylalanine |
| Aad | L-amino adipic acid |
| D-Aad | D-amino adipic acid |
| Orn | Ornithine |
| | Protecting Groups |
| INOC | isonicotinyloxycarbonyl |
| BOC | tert-butyloxycarbonyl |
| OMe | methyl ester |
| CBZ | benzyloxycarbonyl |
| 2-Cl-CBZ | 2-chlorobenzyloxycarbonyl |
| Me | methyl |
| | Activating and Other Groups |
| ONp | p-nitrophenyl ester |
| HSE | N—hydroxysuccinimide ester |
| HBT | 1-hydroxybenzotriazole |
| Ph | Phenyl |
| NMM | N—methylmorpholine |
| | Condensing and Cyclizing Agents |
| DCC | dicyclohexylcarbodiimide |
| DPPA | diphenylphosphorylazide |
| | Reagents |
| TFA | trifluoroacetic acid |
| TEA | triethylamine |
| DIPEA | diisopropylethylamine |
| DMAP | dimethylaminopyridine |
| | Solvents |
| EPAW | ethyl acetate-pyridine-acetic acid-water |
| BAW | butanol-acetic acid-water |
| CMW | chloroform-methanol-water |
| DMF | dimethylformamide |
| THF | tetrahydrofuran |

In accordance with the present invention, the novel cyclic tetrapeptide somatostatin analogs are prepared by cyclizing corresponding linear peptides. The linear peptides are prepared by using the solid phase sequential synthesis technique. Accordingly, the process for preparing the cyclic tetrapeptide somatostatin analogs of the present invention comprises (a) preparing a corresponding blocked linear peptide attached to a solid phase resin; (b) selectively deblocking the N-terminal amine group; (c) removing the linear peptide from the resin; (d) treating the linear peptide with a cyclizing agent to obtain the cyclic tetrapeptide through the formation of an amide bond; (e) selectively removing the side chain blocking groups on the bridging unit; (f) attaching $R_1$ or $R_1'$ with a coupling agent; and (g) removing any side chain blocking groups.

When the linear peptide is prepared on the resin, it is generally not critical which amino acid is selected to be at the C-terminal position provided only that the sequence of amino acids in the linear peptide corresponds to that in the desired somatostatin analog. Once a linear peptide has been cyclized one can no longer determine which amino acid was at the C-terminus of the linear peptide.

While generally the selection of the first amino acid to start the chain is not critical, since the linear peptide will be cyclized, there may be other factors which may prefer one starting amino acid over another. For example D-Trp can react with t-butyl carbonium ions which are formed when BOC groups are removed. Thus, selection of a reaction sequence which places D-Trp at the N-terminal end of the linear peptide will cause D-Trp to be added last, and thus it will have the least exposure to t-butyl carbonium ions. This type of selection may not always be possible, such as where there are two indole containing moieties in the peptide. However, such reaction sensitivities should be considered when planning a peptide reaction sequence.

The synthesis of the linear peptides by the solid phase technique is conducted in a stepwise manner on chloromethylated resin. The resin is composed of fine beads (20–70 microns in diameter) of a synthetic resin prepared by copolymerization of styrene with 1 to 2 percent divinylbenzene. The benzene rings in the resin are chloromethylated in a Friedel-Crafts reaction with chloromethyl methyl ether and stannic chloride. The Friedel-Crafts reaction is continued until the resin contains 0.5 to 5 mmoles of chlorine per gram of resin.

The amino acid selected to be the C-terminal amino acid of the linear peptide is converted to its amino protected derivative. The carboxyl group of the selected C-terminal amino acid is bound covalently to the insoluble polymeric resin support, as the benzyl ester from the resin-bonded benzyl chloride present in chloromethyl-substituted polystyrene-devinylbenzene resin. After the amino protecting group is removed, the amino protected derivative of the next amino acid in the sequence is added along with a coupling agent, such as dicyclohexylcarbodiimide. The amino acid reactant may be employed in the form of a carboxyl-activated amino acid such as the ONp ester, an amino acid azide, and the like. Deprotection and addition of successive amino acids is performed until the desired linear peptide is formed.

The selection of protecting groups is, in part, dictated by particular coupling conditions, in part by the amino acid and peptide components involved in the reaction.

Amino-protecting groups ordinarily employed include those which are well known in the art, for example, urethane protecting substituents such as benzyloxycarbonyl (carbobenzoxy), p-methoxycarbobenzoxy, p-nitrocarbobenzoxy, t-butyloxycarbonyl, and the like. It is preferred to utilize t-butyloxy carbonyl (BOC) for protecting the $\alpha$-amino group in the amino acids undergoing reaction at the carboxyl end of said amino acid. The BOC protecting group is readily removed following such coupling reaction and prior to the subsequent step by the relatively mild action of acids (i.e. trifluoro acetic acid, or hydrogen chloride in ethyl acetate).

The $\alpha$-amino group of Orn can be protected by the CBZ group which is removed by catalytic hydrogenation or by treatment with HF. The $\alpha$-carboxyl group of Aad can be protected as its methyl ester. In the case of Lys, it is preferred to protect the $\epsilon$-amino group with the INOC group as this group is not removed with HF during cleavage of the peptide from the resin or after the peptide has been cyclized. The INOC group may be removed at the end of the synthesis using catalytic hydrogenation or Zn. None of the above groups are affected by TFA, used for removing BOC protecting groups. After the linear peptide is cyclized, the protective group CBZ is removed by treatment with HF, and the methyl ester group is removed by treatment with aqueous NaOH.

After the linear peptide has been formed on the solid phase resin, it may be removed from the resin by a variety of methods which are well known in the art. For example the peptide may be cleaved from the resin with HF and thus directly form the peptide acid which may be subsequently cyclized using a cyclizing agent to the desired cyclic peptide. Suitable reagents for this purpose include DCC or DPPA in the presence of a base such as a tertiary amine, triethyl amine or N-methylmorpholine or sodium bicarbonate. This reaction is carried out in the presence of either water and/or a non-aqueous solvent such as dimethylformamide, tetrahydrofuran, dioxane, chloroform, methylene chloride, etc., at a temperature between about $-40°$ C. and $+20°$ C. Alternatively, the peptide may be removed from the resin by treatment with a lower alcohol such as methanol in the presence of an organic base such as triethylamine, thus resulting in the formation of the corresponding lower alcohol ester of the linear peptide. The resulting ester may be converted to the acid which may then be cyclized, using the cyclizing agent, to the desired cyclic peptide. The preferred method for cleaving the peptide from the resin in the present invention is the use of HF.

As reference Table II will show, one preferred overall procedure for preparing the desired cyclic peptides of the present invention involves the stepwise synthesis of the linear peptide on a solid phase resin. More specifically, in the process for preparing cyclo(D-Trp-Lys-$\delta$-D,L-Aad(NHCH$_2$CH$_2$CH$_2$Ph)Phe) the carboxyl end of the N-blocked amino acid phenylalanine is bound covalently to an insoluble polymeric resin support as the carboxylic acid ester of the resin-bonded benzyl chloride. The amino group of Phe is protected by the BOC group. After the attachment of the (BOC)Phe is completed on the resin, the protecting group BOC is removed by treatment with TFA in CH$_2$Cl$_2$. The subsequent amino acids are attached, in the form of BOC-amino acid, using DCC as the condensing agent. After the desired linear peptide has been prepared, the N-terminal amino group is selectively deblocked and the peptide is removed from the resin by treatment with HF. The resulting linear peptide with the N-terminal amino group deblocked having the amino acid sequence:

D-Trp-Lys(INOC)-$\delta$-D,L-Aad(OCH$_3$)Phe is treated with DPPA at from $-40°$ to 20° C. The linear peptide cyclizes to form:

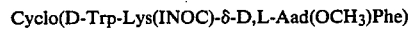

Cyclo(D-Trp-Lys(INOC)-$\delta$-D,L-Aad(OCH$_3$)Phe)

The protecting methyl group on the Aad is removed by treatment with an inorganic base such as sodium hydroxide in a mixture of water and organic solvents such as dioxane or THF.

The R$_1'$ group is substituted on the cyclic tetrapeptide to form compound IIb by reacting the peptide with an acylating reagent such as DCC, DPPA, carbonyldiimidazole and the like, and aminating the acylated intermediate with the appropriate phenylloweralkylamine.

The remaining INOC protecting group is removed by treatment with hydrogen gas in the presence of a metal catalyst such as palladium or platinum on a carbon substrate, in organic solvents such as DMF, ethanol, methanol or ethyl acetate.

The crude cyclic peptide obtained is purified chromatographically, preferably with column chromatography on silica gel. The elution solvent is generally an organic solvent or mixtures thereof which is selected by analyzing aliquots of the material using thin layer chromatography.

TABLE II

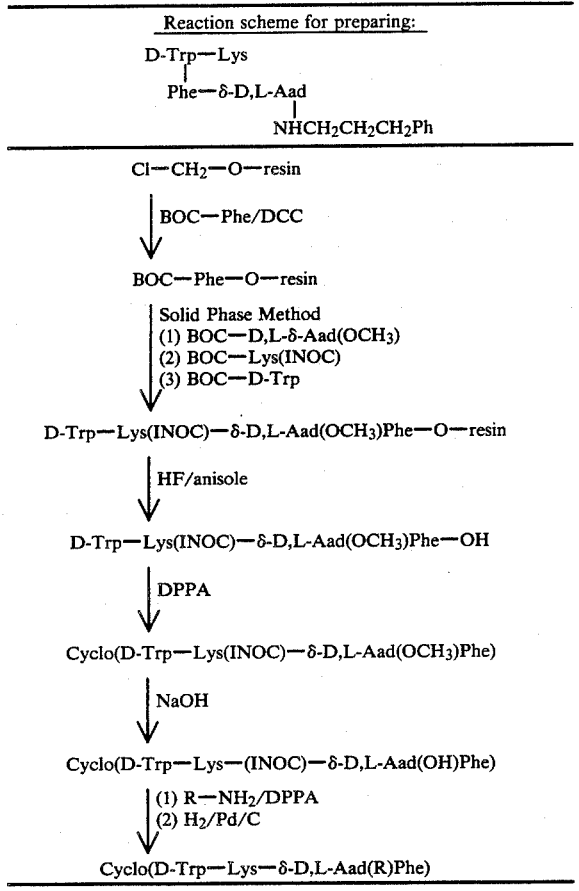

Referring to Table III, another preferred overall procedure for preparing the desired cyclic peptides of the present invention involves the stepwise synthesis of the linear peptide using the mixed anhydride procedure. More specifically, the process shows the preparation of cyclo(Trp-Lys-δ-Orn(COCH₂CH₂CH₂Ph)-Phe).

A solution (0.1 to 1.0M) of a suitably protected BOC amino acid and 1 equivalent of an organic base such as NMM, TEA, DIPEA in a solvent such as methylene chloride, chloroform, DMF, THF, acetonitrile or ethyl acetate is cooled to −40° to 0° C. Then 1.0 to 2.0 equivalents of isobutyl chloroformate or DPPA is added and the mixture allowed to stir in the cold from 10 to 60 minutes. Then 1.0 to 2.0 equivalents of an amino ester hydrochloride (or peptide ester hydrochloride) is added with 1.0 to 2.0 equivalents of an organic or inorganic base such as TEA, NaHCO₃ and the like in one of the solvents described above. The reaction is stirred at −40° to +20° C. for 0.1 to 5.0 hours and worked up in the usual manner to give a BOC protected peptide ester which may be purified using silica gel chromatography or other normal isolation and purification techniques.

The BOC protecting group is removed prior to the reaction with the next amino acid. A solution of the BOC peptide ester in an organic solvent such as ethyl acetate is cooled to −60° to −20° C. and dry HCl gas or another suitable acid is passed through the solution to prepare the hydrochloride, followed by purging with nitrogen gas to remove excess HCl. The peptide ester hydrochloride is obtained using normal isolation techniques.

Additional amino acids are assembled by repeating the above procedure. When the desired amino acids have been incorporated into the peptide, the ester protection is removed by preparing a solution of the peptide ester hydrochloride (0.1 to 1.0M) in a solvent such as a THF, dioxane, DMF, or aqueous methanol, to which is added a base such as sodium hydroxide solution, potassium hydroxide solution, or triethyl amine. The reaction is kept at from 0° to 40° C. for 1.0 to 24 hours, acidified to neutral pH using aqueous acid preferably mineral acids such as dilute hydrochloric acid and worked up in the usual way to give the linear peptide which is ready for cyclization.

Once the linear peptide has been prepared using the above mixed anhydride procedure, the subsequent reactions are substantially the same as those described above for the use and removal of protecting groups, cyclization, addition of the amino acids to the Aad and Orn groups, and the like.

TABLE III

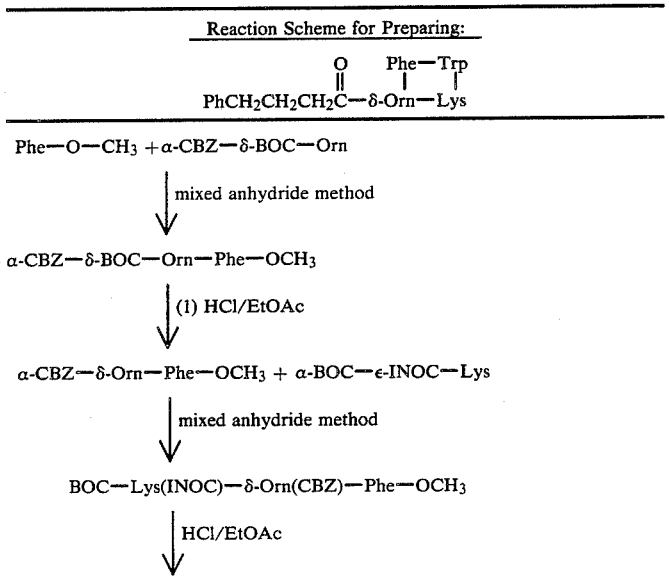

TABLE III-continued

Reaction Scheme for Preparing:

PhCH₂CH₂CH₂C(=O)—δ-Orn(—Phe—Trp)—Lys

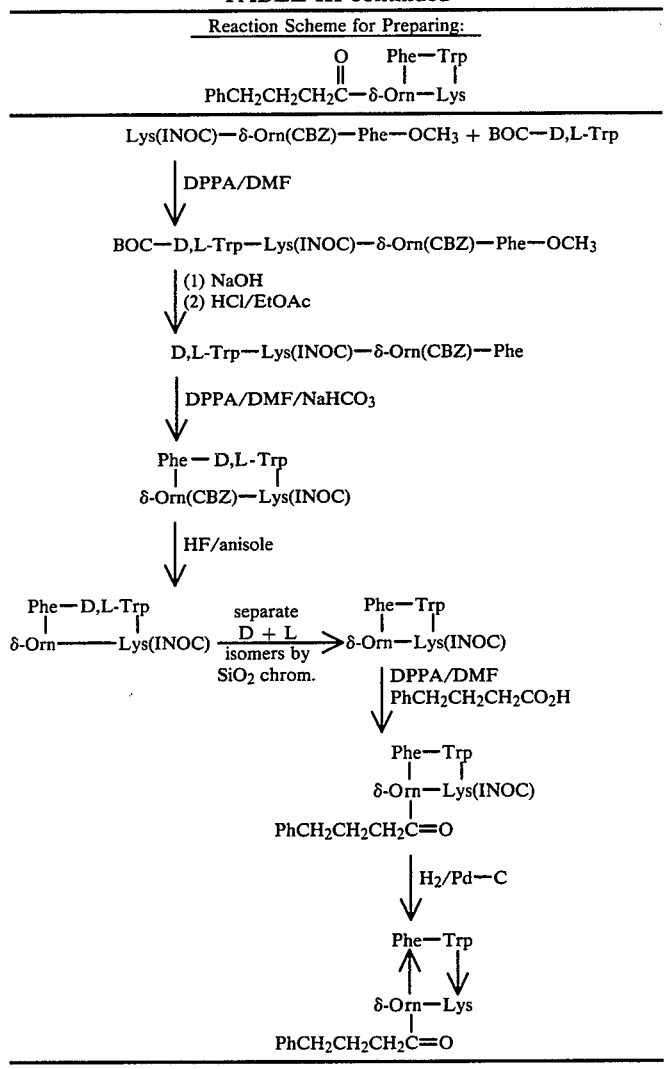

EXAMPLE 1

D-Trp-Lys(INOC)-δ-D,L-Aad(OCH₃)-Phe-O-resin (2)

The solid phase synthesis of the linear tetrapeptide 2 was carried out starting from 7.7 g (9.3 mmol) of BOC-Phe-O-resin (where resin=CH₂-polystyrene 1% cross-linked with p-divinylbenzene) using t-BOC amino acids and a previously reported protocol (Strachan et al., *J. Med. Chem*, 22, 586–588 (1979)) to give 17.5 g of D-Trp-Lys(INOC)-δ-D,L-Aad(OCH₃)-Phe-O-resin.

EXAMPLE 2

D-Trp-Lys(INOC)-δ-D,L-Aad(OCH₃)-Phe-OH

A mixture of 17.5 g (9.3 mmol based on BOC-Phe-O-resin) of the product of Example 1 and 14 ml of anisole was charged to a Kel-F reaction vessel in which approximately 85 ml of anhydrous HF was condensed at −78°. The stirred mixture was warmed to 0° for 30 minutes, and then the HF was removed by water aspirator followed by vacuum pump. The residue was triturated and washed with ether and then dried under reduced pressure. The peptide was leached from the resin by stirring with a mixture of n-butanol and phosphate buffer (pH=7) followed by filtration. The organic layer was twice washed with water and evaporated under reduced pressure to give 6.43 g (89% yield) of D-Trp-Lys(INOC)-δ-D,L-Aad(OCH₃)-Phe-OH as a glassy solid: HPLC 95%, tlc (system C) 0.45 and 0.53, aaa: 1.08 mmol/g; Lys 1.014 (1), Phe 0.986 (1), Aad [1.161 (1)], FABMS M+H 771.

EXAMPLE 3

Cyclo-[D-Trp-Lys(INOC)-δ-D,L-Aad(OCH₃)-Phe]

A stirred solution of 4.41 g (5.71 mmol) of the product of Example 2 in 1.0 L of DMF was degassed under reduced pressure and cooled to −40°, followed by the addition of 1.36 ml (6.30 mmol) of diphenylphosphoryl azide (DPPA) over a 1 minute period. Solid NaHCO₃ (2.4 g) was added in one portion, and the mixture was warmed to 4° and stirred at that temperature for 168 hours. The reaction was worked up by stirring with 225 ml of water and 100 g of AG 501-X8(D) mixed bed resin (Bio-Rad) for 30 minutes. Filtration and removal of the solvents at reduced pressure gave a residue which was triturated with water and dried to give 3.6 g (83% yield) of Cyclo-[D-Trp-Lys(INOC)-δ-D,L-Aad(OCH₃)-Phe] as an amorphous solid: HPLC 89% (280 nm), tlc (system B) 0.62 and 0.65, aaa: 1.303 mmol/g; Lys 1.020 (1), Phe 0.997 (1), Aad 0.982 (1).

EXAMPLE 4

Cyclo-[D-Trp-Lys(INOC)-δ-D,L-Aad(OH)-Phe]

A solution of 1.8 g (2.4 mmol) of the product of Example 3 in 60 ml of 1:2 (v/v) water-dioxane was maintained at pH=10.5–11.0 (as indicated by moistened pH sticks (E. Merck) for 24 hours by the periodic addition of 1.0M NaOH. The pH was then adjusted to 6.0 with 2.0M HCl and the solvents removed at reduced pressure to give a residue which was triturated with water and dried to give 1.21 g (68% yield) of Cyclo-[D-Trp-Lys-(INOC)-δ-D,L-Aad(OH)-Phe] as an amorphous solid which was used directly in the subsequent reactions: tlc (system D) 0.55 and 0.62.

EXAMPLE 5

Cyclo-[D-Trp-Lys-δ-D,L-Aad(R)-Phe] (A–F), general procedure

A stirred solution of 500 mg (0.67 mmol) of the product of Example 4 in 16 ml of DMF was degassed at reduced pressure and cooled to −20° under $N_2$. After adding 0.17 ml (0.8 mmol) of DPPA, the solution was stirred for 8 minutes, followed by the addition of 0.83 mmol of either (a) benzylamine, (b) 2-phenylethylamine, or (c) 3-phenylpropylamine, and 0.34 g of $NaHCO_3$. The solution was warmed to 4° and stirred at that temperature for 42 hours, diluted with 50 ml of 4:1 (v/v) DMF-$H_2O$ and stirred at 20° for 1 hour with 1.0 g of mixed bed resin. The mixture was filtered and the solvents removed to give a solid residue which was dissolved in 80 ml of DMF and added to a $N_2$ filled flask containing 300 mg of 10% Pd/C. The mixture was degassed under reduced pressure and $H_2$ was then introduced into the evacuated flask using a balloon. After stirring under $H_2$ for 18 hours, the catalyst was filtered, washed, and the solvents removed under reduced pressure to afford a residue which was chromatographed on 150 g of $SiO_2$ with 85:14:1.5 followed by 80:20:2 (v/v/v) $CHCl_3$—$CH_3OH$-concentrated $NH_4OH$. Combination, evaporation and lyophilization of the appropriate fractions from 1:9 (v/v) HOAc-$H_2O$ gave approximately 100 mg yields of product A–C as the higher Rf isomers and similar amounts of Product D–F as the lower Rf isomers. Proton nmr spectra and amino acid analyses for Lys, Phe, and Aad were consistent with the assigned structures, and other analytical data are listed in Table IV.

TABLE IV

Analytical data for cyclo-[D-Trp-Lys-X-Phe]acetate salts

TABLE IV

Analytical data for cyclo-[D-Trp—Lys—X—Phe] acetate salts

| Compd. | X | Pept. Cont. μmol/mg | FABMS M + H | HPLC |
|---|---|---|---|---|
| A | δ-Aad(NHCH$_2$—C$_6$H$_5$) | 1.24 | 694 | 97% |
| B | δ-Aad[NH(CH$_2$)$_2$—C$_6$H$_5$] | 1.14 | 708 | 95% |
| C | δ-Aad[NH(CH$_2$)$_3$—C$_6$H$_5$] | 1.20 | 722 | 95% |
| D | δ-D-Aad(NHCH$_2$—C$_6$H$_5$) | 1.07 | 694 | 92% |
| E | δ-D-Aad[NH(CH$_2$)$_2$—C$_6$H$_5$] | 1.08 | 708 | 95% |
| F | δ-D-Aad[NH(CH$_2$)$_3$—C$_6$H$_5$] | 1.16 | 722 | 97% |

EXAMPLE 6

Lys(INOC)-δ-Orn(CBZ)-Phe-OCH$_3$

A solution of 5.04 g (13.8 mmol) of α-CBZ-δ-BOC-ornithine in 50 ml of EtOAc was cooled to −5° C. and 1.61 ml (14.6 mmol) of N-methylmorpholine and 2.0 ml (14.8 mmol) of isobutyl chloroformate were added. After stirring the mixture for 20 minutes, 3.45 g (16 mmol) of phenylalanine methyl ester hydrochloride and 2.0 ml of NMM were added. The mixture was stirred at −5° for 1½ hours, diluted with 50 ml of EtOAc, and stirred for an additional 1 hour. The mixture was extracted with three portions of 0.5M citric acid, two portions of 5% NaHCO$_3$, saturated NaCl, and dried over Na$_2$SO$_4$. Removal of the solvents at reduced pressure gave 7.34 g of a colorless solid. This material was dissolved in 200 ml of EtOAc and cooled to −40° and treated with HCl gas which caused the temperature to rise to −10° C. After 5 minutes, the HCl was stopped, and the solution purged with N$_2$ for 30 minutes while warming to 0° C. The resulting precipitate was washed with ether and dried at reduced pressure to give 5.35 g (84%) of a colorless solid α-Orn-(CBZ)-Phe-OCH$_3$.

A solution of α-BOC-ε-INOC-Lys in 120 ml of 5:5:2 EtOAc-CH$_3$CN-DMF was cooled to −10° with 1.43 ml (13 mmol) of NMM. 1.68 Ml (13 mmol) of isobutyl chloroformate was added and the mixture stirred for 10 minutes. Then 5.3 g (11.4 mmol) of α-CBZ-δ-Orn-Phe-OCH$_3$ was added along with 1.25 ml (11.4 mmol) of NMM. After stirring for 3 hours at −10° to +10° C., the mixture was diluted with 200 ml EtOAc and washed twice with 0.5M citric acid, twice with 5% NaHCO$_3$, saturated NaCl, and dried over Na$_2$SO$_4$. Removal of the solvents at reduced pressure gave 6.0 g (66%) of a yellow glass. A solution of this material in 300 ml of EtOAc was treated with HCl gas as described above to give 5.34 g (92%) of Lys(INOC)-δ-Orn(CBZ)-Phe-OCH$_3$.

EXAMPLE 7

D,L-Trp-Lys(INOC)-δ-Orn(CBZ)-Phe

A solution of 2.74 g (9.0 mmol) of BOC-D,L-Trp in 50 ml of degassed DMF was added 1.94 ml (9.0 mmol) of DPPA at −25° C. After 10 minutes, 5.32 g (7.0 mmol) of Lys(INOC)-δ-Orn(CBZ)-Phe-OCH$_3$ was added, followed by 3.8 g of NaHCO$_3$. The mixture was stirred at 4° C. for 6 days, quenched with 10 ml of H$_2$O and the solvents removed under reduced pressure. The residue was triturated with 200 ml of H$_2$O to give 6.9 g of a solid. This solid was dissolved in 100 ml of 2:1 dioxane-H$_2$O and treated with 2.0M NaOH to maintain a pH of 11–12 for 17 hours. The mixture was acidified to pH=6.2 with 2.0M HCl, and the solvents removed at reduced pressure. The residue was suspended in 200 ml of EtOAc and treated with HCl gas as above to give 9.0 g of D,L-Trp-Lys(INOC)-δ-Orn(CBZ)-Phe.

EXAMPLE 8

Cyclo(D,L-Trp-Lys(INOC)-δ-Orn(CBZ)-Phe

A solution of the product from Example 7 was dissolved in 1.1 L of degassed DMF and cooled to 20° C. Then 1.72 ml (8 mmol) of DPPA was added, followed by 3.36 g of NaHCO$_3$. The reaction was stirred at 4° C. for 3 days, quenched with 200 ml of H$_2$O, and the solvents removed under reduced pressure. The residue was triturated with 300 ml of H$_2$O to give 5.5 g of a solid identified as cyclo(D,L-Trp-Lys(INOC)-δ-Orn(CBZ)-Phe.

EXAMPLE 9

Cyclo(D,L-Trp-Lys(INOC)-δ-Orn-Phe)

5.14 G of the product from Example 8 were treated with 73 ml of 9:1 HF-anisole for 1¼ hours at 0° C., then the HF was removed at reduced pressure. The residue was triturated with Et₂O-petroleum-ether and dried to give a solid which was chromatographed on silica gel using 80:20:2 CHCl₃—LCH₃OH—NH₄OH to give 0.9 g of each isomer of cyclo(Trp-Lys(INOC)-δ-Orn-Phe) and cyclo(D-Trp-Lys(INOC)-δ-Orn-Phe).

EXAMPLE 10

Cyclo(Trp—Lys(INOC)—δ-Orn(CCH₂CH₂CH₂Ph)—Phe)

A solution of 66 mg (0.4 mmol) of phenylbutyric acid in 5 ml of degassed DMF was cooled to −5° and 86 μl (0.4 mmol) of DPPA was added, followed by cyclo(Trp-Lys(INOC)-δ-Orn-Phe) 150 mg (0.21 mmol) and 168 mg of NaHCO₃. After stirring at 4° C. for 3 days, 10 ml of H₂O was added and the solvents removed under reduced pressure. The residue was triturated with H₂O to give 0.2 g of a solid identified as cyclo(Trp-Lys-(INOC)-δ-Orn(COCH₂CH₂CH₂Ph)-Phe).

EXAMPLE 11

Cyclo(Trp-Lys-δ-Orn(COCCH₂CH₂CH₂Ph)-Phe)

A N₂ filled flask was charged with the material from Example 10 and 0.2 g of 10% palladium on carbon. The mixture was then slurried in 50 ml of degassed DMF, evacuated, and kept under an H₂ atmosphere for 16 hours. The reaction mixture was diluted with 150 ml of 8:1 EtOH-HOAc (50%), filtered, and the filtrate evaporated to dryness. The residue was chromatographed on silica gel using 80:20:2 CHCl₃—CH₃OH—NH₄OH to give 83 mg of cyclo(Trp-Lys-δ-Orn(COCH₂CH₂CH₂Ph)-Phe). HPLC (97%) FABMS M+H=722.

EXAMPLE 12

Four studies were conducted on urethane-anesthetized male CD rats in order to determine the potency of the compounds relative to somatostatin in modifying plasma levels of insulin and glucagon. The compounds were administered intravenously via the jugular vein. The rats were bled portally 5 minutes after the compounds were injected. Insulin and glucagon RIA's were conducted on the plasma samples.

Male CD rats were anesthetized with urethane and were bled via the orbital sinus after 20 minutes to provide basal (0 time point) blood glucose values. Immediately following the bleeding, groups containing 6 rats were administered water, compound E or test compound via the saphenous vein. The rats were subsequently orbitally bled at various time points. Each blood sample was analyzed for blood glucose content using the Technicon alkaline potassium ferricyanide procedure.

When the foregoing tests were carried out on compound F from Table IV, at a dose of 500 μg per mouse, there was at 15 minutes after dosing a 130%, and at 30 to 90 minutes after dosing a 150% level of blood glucose compared to the basal blood glucose level. Significant increases of blood glucagon levels were also noted.

What is claimed is:

1. A compound having the formula:

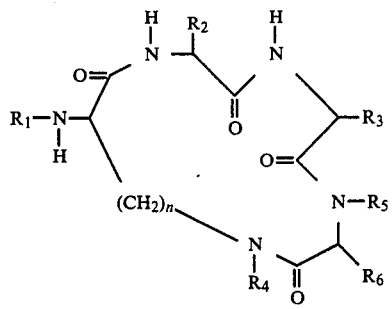

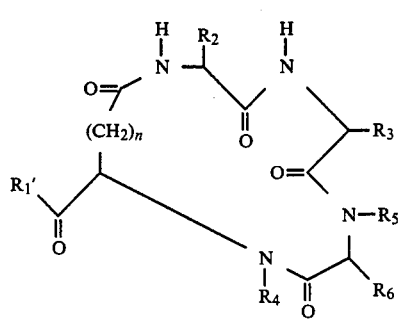

wherein:
n is 0 to 4;
R₁ is phenylloweralkanoyl, or an amino acid

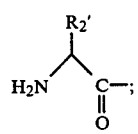

R₁' is phenylloweralkylamino, or an amino acid

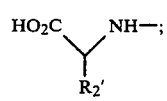

R₂ and R₂' are loweralkyl, benzyl, naphthylmethyl, indolylmethyl, substituted benzyl where the substituent may be one or two of loweralkyl, halogen, hydroxy, amino, nitro or loweralkoxy; and loweralkyl substituted with a 5- or 6-membered heterocyclic ring;
R₃ is 3-indolylmethyl, naphthylmethyl or substituted 3-indolylmethyl wherein the substituent may be loweralkyl, loweralkoxy, or halogen;
R₄ and R₅ are independently hydrogen or methyl
R₆ is aminocyclohexylmethyl, aminomethylbenzyl or

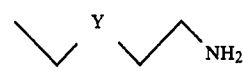

wherein Y is (CH₂)ₘ and m is 0, 1 or 2 or sulfur such that the sulfur may be in any position along the chain.

2. A compound of claim 1 wherein:

n is 3;
R$_1$, R$_1$' and R$_2$ are as defined in claim 1;
R$_3$ is 3-indolylmethyl;
R$_4$ and R$_5$ are hydrogen; and
R$_6$ is —CH$_2$CH$_2$CH$_2$CH$_2$NH$_2$.

3. The compound of claim 2 wherein R$_1$ is phenylloweralkanoyl, or an amino acid wherein R$_2$' is benzyl; R$_1$' is phenylloweralkylamino or an amino acid wherein R$_2$' is benzyl; and R$_2$ are loweralkyl, benzyl or substituted benzyl where the substituent is loweralkyl, halogen, hydroxy, amino, nitro or alkoxy.

4. The compound of claim 2 which is cyclo(D-Trp-Lys-δ-Aad(NHCH$_2$-Ph)-Phe).

5. The compound of claim 2 which is cyclo(D-Trp-Lys-δ-Aad(NH(CH$_2$)$_2$-Ph)-Phe).

6. The compound of claim 2 which is cyclo(D-Trp-Lys-δ-Aad(NH(CH$_2$)$_3$-Ph)-Phe).

7. The compound of claim 2 which is cyclo(D-Trp-Lys-δ-D-Aad(NH$_2$CH$_2$-Ph)-Phe).

8. The compound of claim 2 which is cyclo(D-Trp-Lys-δ-D-Aad(NH$_2$(CH$_2$)$_2$-Ph)-Phe).

9. The compound of claim 2 which is cyclo(D-Trp-Lys-δ-Aad(NHCH$_2$CH$_2$CH$_2$Ph)-Phe).

10. The compound of claim 2 which is cyclo(D-Trp-Lys-δ-D-Aad(NH$_2$(CH$_2$)$_3$-Ph)-Phe).

11. The compound of claim 2 which is cyclo(Trp-Lys-δ-Orn(COCH$_2$CH$_2$CH$_2$Ph)Phe).

12. A method for selectively increasing the levels of blood glucose in an animal which comprises administering to said animal an effective amount of a compound of claim 1.

13. A pharmaceutical composition comprising a therapeutically effect amount of the cyclic hexapeptide of claim 1 or the non-toxic acid addition salts thereof in a pharmaceutically acceptable liquid or solid carrier.

* * * * *